(12) United States Patent
Axelrod et al.

(10) Patent No.: US 10,499,829 B2
(45) Date of Patent: Dec. 10, 2019

(54) WEARABLE WIRELESS PATCHES CONTAINING ELECTRODE PAIR ARRAYS FOR GASTROINTESTINAL ELECTRODIAGNOSTICS

(71) Applicant: G-TECH MEDICAL, INC., Mountain View, CA (US)

(72) Inventors: Steve Axelrod, Los Altos, CA (US);
Anand Navalgund, San Jose, CA (US);
Eric A. Hoffman, Saratoga, CA (US)

(73) Assignee: G-Tech Medical, Inc., Mountain View, CA (US)

( * ) Notice: Subject to any disclaimer, the term of this patent is extended or adjusted under 35 U.S.C. 154(b) by 0 days.

(21) Appl. No.: 15/919,578

(22) Filed: Mar. 13, 2018

(65) Prior Publication Data
US 2018/0199849 A1 Jul. 19, 2018

Related U.S. Application Data

(63) Continuation of application No. 14/051,440, filed on Oct. 10, 2013, now Pat. No. 9,943,264.
(Continued)

(51) Int. Cl.
*A61B 5/0488* (2006.01)
*G16H 10/40* (2018.01)
(Continued)

(52) U.S. Cl.
CPC ........ *A61B 5/04884* (2013.01); *A61B 5/0006* (2013.01); *A61B 5/0024* (2013.01);
(Continued)

(58) Field of Classification Search
CPC . A61B 5/04884; A61B 5/0006; A61B 5/0024; A61B 5/04014; A61B 5/0402;
(Continued)

(56) References Cited

U.S. PATENT DOCUMENTS 5,704,368 A 1/1998 Asano et al.
5,795,304 A 8/1998 Sun et al.
(Continued)

FOREIGN PATENT DOCUMENTS

WO 199610358 A1 4/1996
WO 2010068818 A2 6/2010
(Continued)

OTHER PUBLICATIONS

Haddab, S. et al. "Microcontroller-Based System for Electrogastrography Monitoring Through Wireless Transmission"; Measurement Science Review, vol. 9, No. 5, 2009, p. 122-126.
(Continued)

*Primary Examiner* — Daniel L Cerioni
(74) *Attorney, Agent, or Firm* — Aurora Consulting LLC; Ashley Sloat

(57) ABSTRACT

A system and method for profiling electrical activity in smooth muscle of the gastrointestinal tract muscular of a patient are disclosed. The system includes electromyographic-sensing patches adapted for placement on the skin of the abdomen of the patient. Each patch has at least one bipolar electrode pair, or a multitude arranged in an array, and is enabled for communication of a signal indicative of a sensed electromyographic signal. The system further includes networked computing devices. The local patch device is configured for wireless communication between the EMG-sensing patches and a local computing device, to enable wireless transmission from the patch to the networked computing devices. The networked computing device is configured to process large aggregate collections of multi-hour or day signals received from the local computing device to yield diagnostically valuable physiological parameters of gastrointestinal smooth muscle electrical activity.

16 Claims, 6 Drawing Sheets

Related U.S. Application Data

(60) Provisional application No. 61/712,100, filed on Oct. 10, 2012.

(51) Int. Cl.

| | | |
|---|---|---|
| *A61B 5/00* | (2006.01) | |
| *G16H 50/20* | (2018.01) | |
| *A61B 5/11* | (2006.01) | |
| *A61B 5/04* | (2006.01) | |
| *A61B 5/0492* | (2006.01) | |
| *A61B 5/08* | (2006.01) | |
| *A61B 5/0476* | (2006.01) | |
| *A61B 5/0402* | (2006.01) | |
| *G16H 10/60* | (2018.01) | |
| *G16H 40/63* | (2018.01) | |
| *G16H 40/67* | (2018.01) | |
| *G16H 50/70* | (2018.01) | |

(52) U.S. Cl.
CPC ........ *A61B 5/0402* (2013.01); *A61B 5/04014* (2013.01); *A61B 5/0476* (2013.01); *A61B 5/0492* (2013.01); *A61B 5/08* (2013.01); *A61B 5/1107* (2013.01); *A61B 5/1123* (2013.01); *A61B 5/42* (2013.01); *A61B 5/4205* (2013.01); *A61B 5/4211* (2013.01); *A61B 5/6823* (2013.01); *A61B 5/6831* (2013.01); *A61B 5/6833* (2013.01); *A61B 5/7203* (2013.01); *G16H 10/40* (2018.01); *G16H 10/60* (2018.01); *G16H 40/63* (2018.01); *G16H 40/67* (2018.01); *G16H 50/20* (2018.01); *G16H 50/70* (2018.01); *A61B 5/11* (2013.01); *A61B 2562/0209* (2013.01); *A61B 2562/04* (2013.01); *A61B 2562/164* (2013.01)

(58) Field of Classification Search
CPC ...... A61B 5/0476; G16H 10/40; G16H 10/60; G16H 50/20
USPC ........................................................ 600/546
See application file for complete search history.

(56) References Cited

U.S. PATENT DOCUMENTS

| | | | |
|---|---|---|---|
| 5,857,980 | A | 1/1999 | Wilson |
| 6,351,665 | B1 | 2/2002 | Koch |
| 7,160,254 | B2 | 1/2007 | Noar |
| 7,593,768 | B1 | 9/2009 | Vasilev et al. |
| 9,955,914 | B2 | 5/2018 | Dunki-Jacobs et al. |
| 2003/0069714 | A1 | 4/2003 | Wigley et al. |
| 2004/0260164 | A1 | 12/2004 | Kilcoyne et al. |
| 2005/0075578 | A1* | 4/2005 | Gharib ................ A61B 5/0492 600/546 |
| 2005/0209709 | A1 | 9/2005 | Bradshaw |
| 2005/0215917 | A1 | 9/2005 | Noar |
| 2006/0058606 | A1 | 3/2006 | Davis et al. |
| 2006/0107954 | A1 | 5/2006 | Katz et al. |
| 2006/0149541 | A1 | 7/2006 | Jaklitsch et al. |
| 2006/0258927 | A1 | 11/2006 | Edgar, Jr. et al. |
| 2007/0150007 | A1* | 6/2007 | Anderson ................ A61N 1/05 607/2 |
| 2007/0225576 | A1 | 9/2007 | Brown et al. |
| 2007/0287931 | A1 | 12/2007 | Dilorenz |
| 2008/0154110 | A1 | 6/2008 | Burnes et al. |
| 2008/0281312 | A1* | 11/2008 | Werneth ............. A61B 18/1492 606/33 |
| 2009/0318783 | A1 | 12/2009 | Rohde et al. |
| 2010/0172839 | A1 | 7/2010 | Walker |
| 2010/0228105 | A1 | 9/2010 | Policker et al. |
| 2010/0292606 | A1 | 11/2010 | Prakash et al. |
| 2012/0209102 | A1* | 8/2012 | Ylotalo ................ A61B 5/0006 600/397 |
| 2013/0046150 | A1 | 2/2013 | Devanaboyina |
| 2014/0206976 | A1* | 7/2014 | Thompson ........... A61B 5/0006 600/391 |
| 2014/0226158 | A1 | 8/2014 | Trainer |
| 2016/0121111 | A1 | 5/2016 | Levine et al. |

FOREIGN PATENT DOCUMENTS

| | | |
|---|---|---|
| WO | 2010121038 A1 | 10/2010 |
| WO | 2012060874 A2 | 5/2012 |

OTHER PUBLICATIONS

Chen, JDZ et al.; "Detection of gastric slow wave propagation from the cutaneous electrogastrogram"; Am. J. Physiol. 277 (Gastronintest. Liver Physiol. 40): G424-G430, 1999.

Kim, D, W; et al. "Usefulness of a Developed Four-Channel EGG System with running spectrum analysis"; Yonsei Medicl Journal; vol. 41; No. 2; 2000; 230-236.

Garcia-Casado, J. et al.; "Noninvasive Measurement and Analysis of Intestinal Myoelectrical Activity Using Surface Electrodes" IEEE Transactions on Biomedical Engineering, vol. 52, No. 6, Jun. 2005; p. 983-991.

Chen, J.D. Z. et al; "Measurement of Electrical Activity of the Human Small Intestine Using Surface Electrodes"; IEEE Transactions on Biomedical Engineering, vol. 40, No. 6, Jun. 1993; p. 598-602.

Lammers, W. J. E. P et al; "Orgin and propagation of the slow wave in the canine stomach: the outlines of a gastric conduction system" Am J Physiol Gastrointest Liver Physiol 296: G1200-G1210, 2009.

Leahy, A. et al.; "Abnormalities of the Electrogastrogram in Functional Gastrointestinal Disorders"; American Journal of Gastroenterology; vol. 94, No. 4, 1999; pp. 1023-1028.

Myers, T. J. et al; "Human Surface Electrogastrograms: AC and DC measurements"; Annals of Biomedical Engineering, vol. 12, pp. 319-333, 1984.

Wang, Z. S. et al.; "Detection of gastric slow wave uncoupling from multi-channel electrogastrogram: validations and applications"; Neurogastroenterol Motil (2003) 15, 457-465.

Written Opinion issued on PCT Application Serial No. PCT/US2011/01848 by ISA/US dated May 21, 2012, pp. 1-5.

International Search Report issued on PCT Application Serial No. PCT/US2011/01848 by ISA/US dated May 21, 2012, pp. 1-4.

International Search Report and Written Opinion issued for PCT/US2015/056282 by ISA/US dated Jan. 20, 2016 (9 pages).

"Home-ePatch." DELTA Danish Electronics, Light & Acoustics. Available at: http://epatch.madebydelta.com. Accessed: Jul. 1, 2016.

Haahr, R. et al. "A wearable 'electronic patch' for wireless continuous monitoring of chronically diseased patients," 5th International Summer School and Symposium on Medical Devices and Biosensors, 2008, pp. 66-70.

Sanders, K. M. et al. "Interstitial cells of Cajal as pacemakers in the gastrointestinal tract"; Annu. Rev. Physiol. 2006. 68:307-343.

Madsen et al., "Listening to Bowel Sounds: An Evidence-Based Practice Project," Dec. 2005, AJN, vol. 105, No. 12, p. 40-48.

Biopac Systems, Inc., "Bipolar EEG" website page.

De Luca et al., "Inter-electrode spacing of surface EMG sensors: Reduction of crosstalk contamination during voluntary contractions," Journal of Biomechanics (2011), doi: 10.1016/j.jbiomech2011.11.010.

Puurtinen et al., "Best Electrode Locations for a Small Bipolar ECG Device: Signal Strength Analysis of Clinical Data," Annuals of Biomedical Engineering, vol. 37, No. 2, Feb. 2009 pp. 331-336, DOI: 10.1007/s10439-008-9604-y.

* cited by examiner

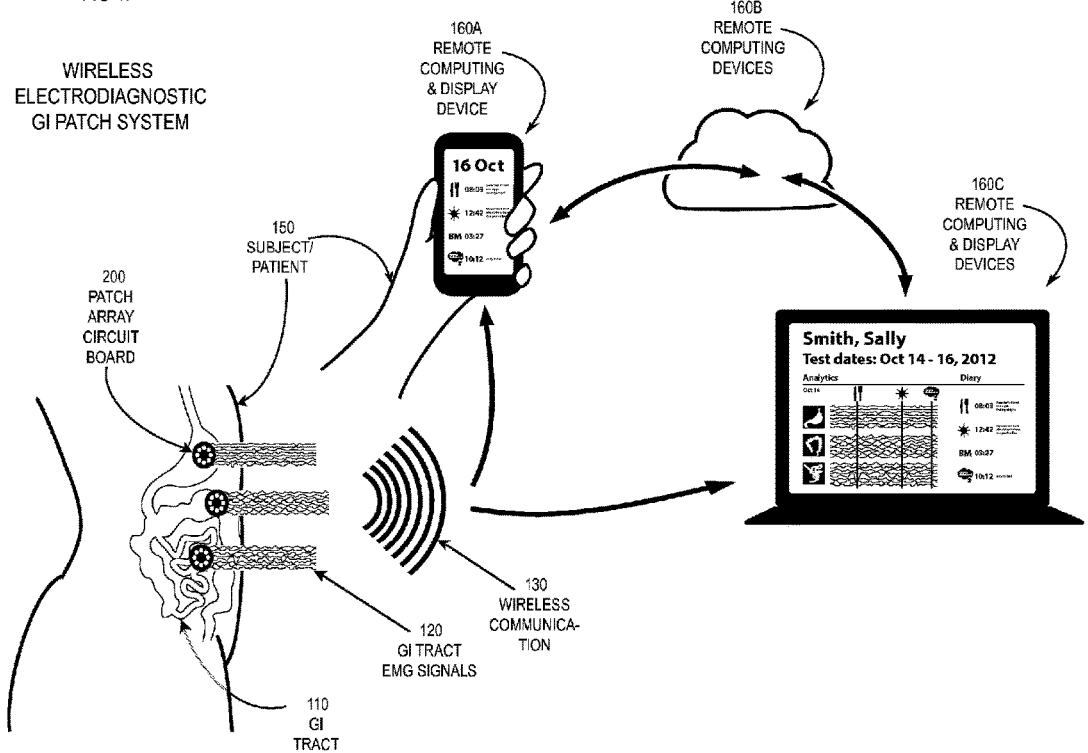

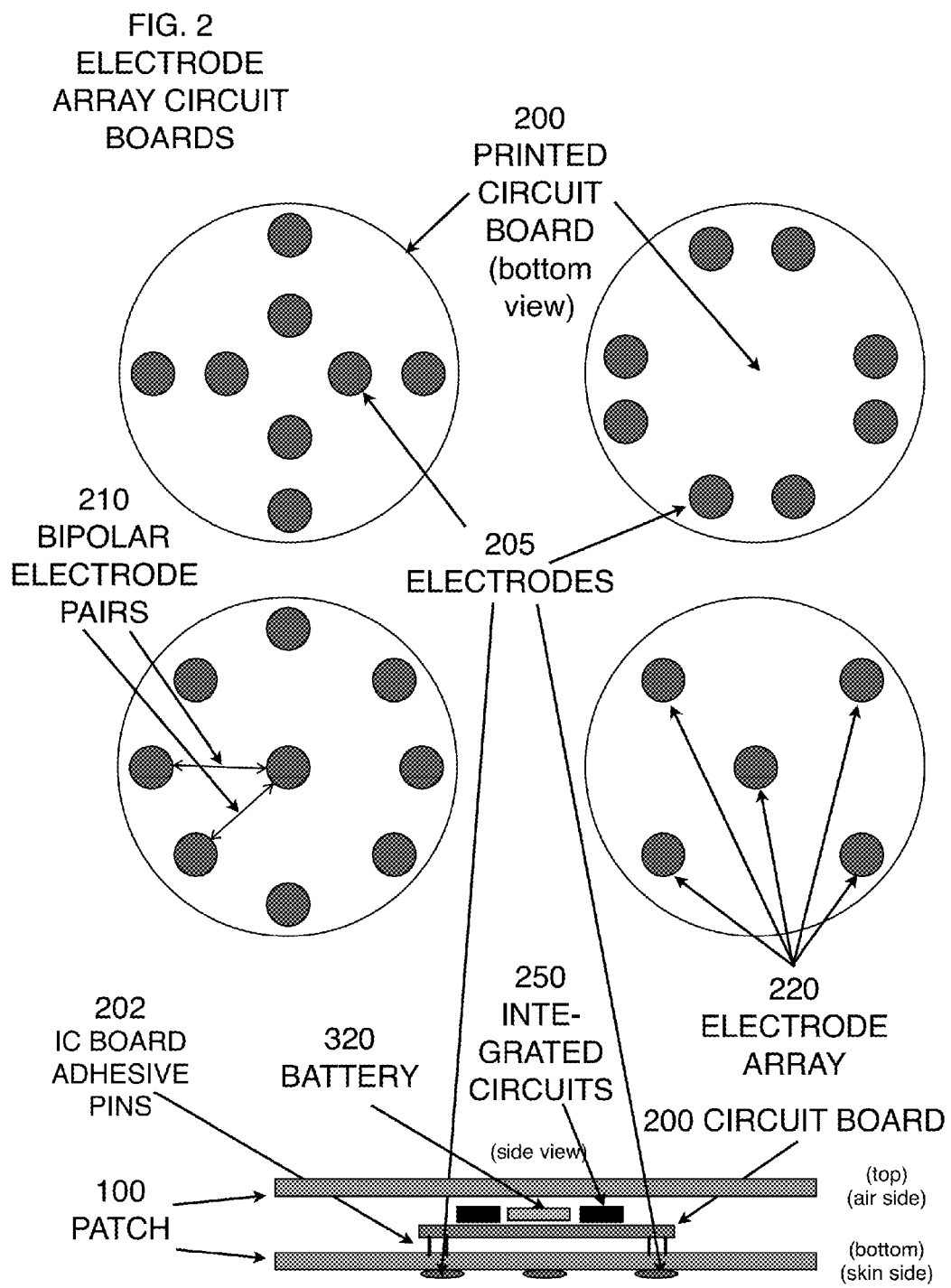

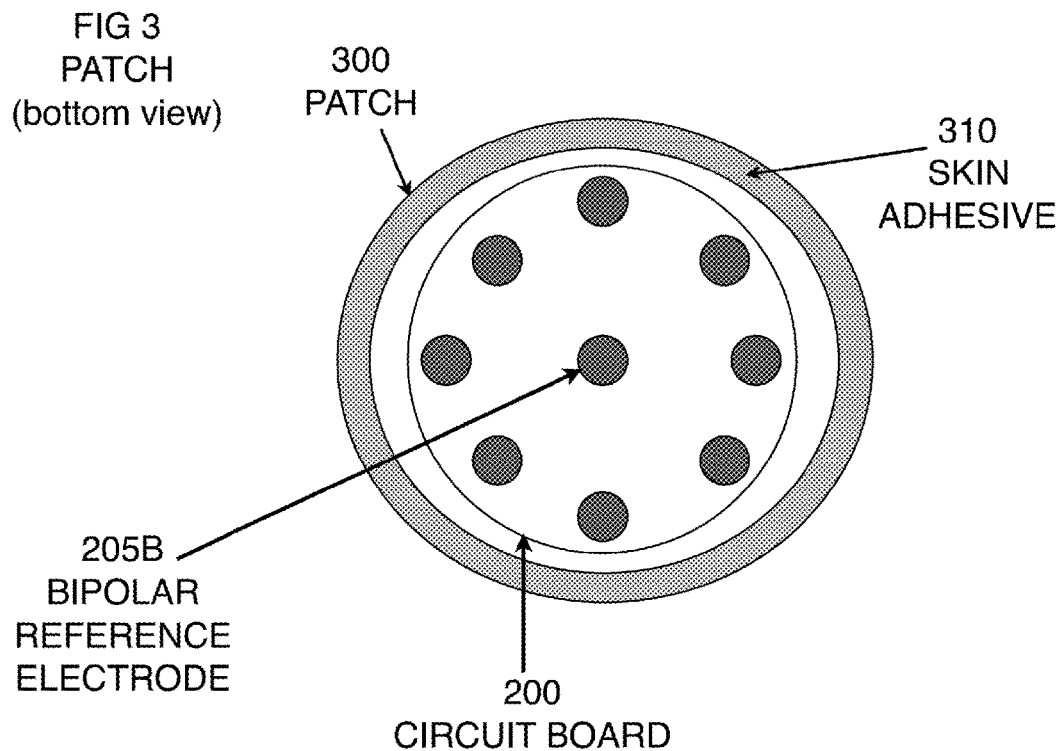
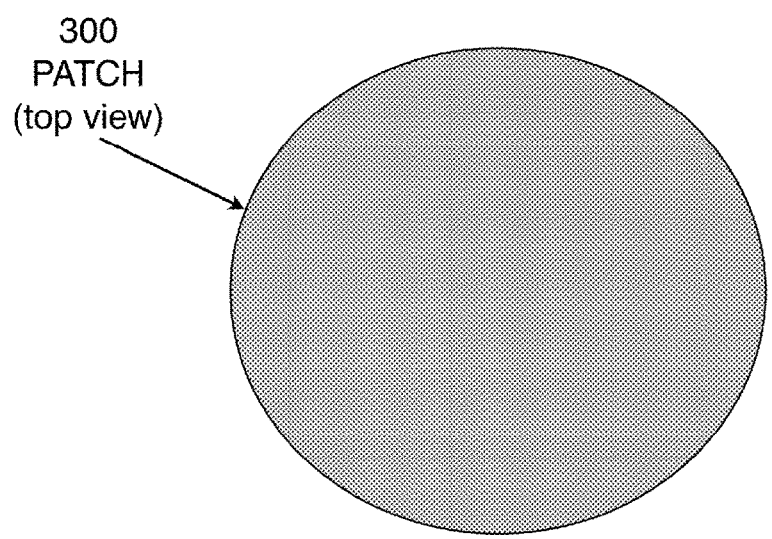

WEARABLE WIRELESS PATCHES CONTAINING ELECTRODE PAIR ARRAYS FOR GASTROINTESTINAL ELECTRODIAGNOSTICS

CROSS-REFERENCE TO RELATED APPLICATIONS

This application is a continuation of U.S. patent application Ser. No. 14/051,440, filed Oct. 10, 2013, now issued as U.S. Pat. No. 9,943,264 on Apr. 17, 2018, which claims the benefit of U.S. Provisional Patent Application Ser. No. 61/712,100, filed Oct. 10, 2012, the contents of both of which are herein incorporated by reference in their entireties.

TECHNICAL FIELD

This disclosure relates generally to electromyographic (EMG) and electrodiagnostic systems and methods for profiling electrical activity within the smooth muscle of the gastrointestinal tract, and more particularly to systems and methods for mathematically extracting salient patterns of diseased electromyographic activity of the gastrointestinal tract from gathering large data sets of multi-hour and multi-day recordings from ambulatory patients with wearable, disposable, wirelessly-enabled sensor patches, and for diagnosing various gastrointestinal disorders. The disclosed invention can further be used in gastrointestinal drug research and discovery, and for possible treatments of certain GI tract disorders.

BACKGROUND

The majority of gastrointestinal motility tests are invasive and a source of much discomfort and patient anxiety and expense. Therefore, advancing the state of the art in noninvasive technologies is highly desired. The present invention utilizes combinations of electrogastrography and electroenterography (EGG & EEnG), both of which allow for noninvasive and potentially long term ambulatory data collection of patients, which in turn provides for greater patient convenience and comfort, lower costs, and more powerful diagnostic potential. EGG captures the rhythmical electrical activity of the stomach through electrodes located on the abdomen in the vicinity of the stomach, while EEnG captures the intestinal slow muscle electrical activity which may present anywhere on the abdomen.

Methods and systems for obtaining EMG data from the gastrointestinal tract of patients, particularly patients who appear to suffer from disorders related to gastrointestinal motility, are known in the prior art and practiced by specialists in the art. Such systems and methods typically are used in a procedure that occurs in a clinical setting, within a time frame of several hours, and wherein the patient needs to be substantially in repose. Further, the testing procedure usually asks the patient to adhere to a preliminary schedule of eating, and of eating a standardized meal. Finally, the typical electrographic measuring system is only taking measurements from a very small set of EMG bipolar electrodes, typically two or three, and thus measuring just a small sample of the entire gastrointestinal system, while using a large, extremely expensive, typical medical office Electrodiagnostic signal amplification and data acquisition machine.

These constraints, however practical and appropriate, nevertheless likely limit the scope of data derived from such studies. The data are limited in GI tract coverage and time frame. A study is only feasible for several hours, during which a patient can tolerate or comply with the constraint on normal physical activity. This limitation should be understood against the perspective that, in reality, gastrointestinal activity occurs in the context of a daily cycle, and that daily cycle occurs in the context of activities of daily living. Gastrointestinal pain or discomfort also can be cyclical or chaotically intermittent throughout the day, or over the course of several days. Such intermittency may or may not be obviously tied to activities associated with the gastrointestinal tract specifically, or the more general and varied activities of daily living. Accordingly, it is proposed and likely that the diagnostic value of gastrointestinal activity data derived from tests that include such constraints has always been limited in its potential, thus greatly limiting the adoption and use of this field of GI diagnostic technology.

Further, such a gastrointestinal EMG study, as currently practiced, is expensive in that it occupies space in the clinic, and it occupies the time of the healthcare provider who is administering the testing procedure. As a consequence of a cost that limits the prevalence of such testing, the testing is generally applied to severe cases of gastrointestinal distress or to cases that are otherwise difficult to diagnose. And further still, the limited use of such testing limits the accumulation of data as a whole, which would advance understanding of the relationship between dysfunctional gastrointestinal electrical activity and gastrointestinal disorders.

Thus, there is a strong need in the medical marketplace for systems and methods that are more affordable, and which provide a more comprehensive view of gastrointestinal activity throughout a day or for longer periods, and which can monitor such activity while the patient is free to conduct the normal activities of daily living.

There are many examples in the prior art of remote, ambulatory, monitoring, recording and alarm EMG (and other medical sensor) systems. Although the presently disclosed system can include those functions, it is not the ideal objective and embodiment of this invention.

Instead, it is further a novel objective of the ideal embodiment of the present invention to allow for the easy and inexpensive collection of large spatial (skin attachable patches with distributed arrays of inexpensive orthogonal bipolar electrodes allowing coverage over the entire, or large sections, of the midsection) and temporal (overtime, ambulatory subjects going about their normal lives for hours to days) data sets.

All of the currently encountered prior art do not discuss concurrent multi-organ recordings, nor discuss whole digestive track, multi-day recordings for the purposes of GI tract disorder diagnosis. It is furthermore strongly suggested that the presently included invention is not wholly meant as a real-time monitor, since ideal embodiments will entail intermittent patch data storage and transmission in order to optimize battery life.

Additionally, the current state of the art generally allows for a few electrodes, without clear guidance on exact placement or spacing on the body, and recordings made in office for, at most, a few hours. The presently known art also teaches wearable EMG devices for continuous status monitoring, real-time disease event alarms, or personal health data recording. For example, in US patent application 20130046150, titled, Method for diagnosis and treatment of disorders of the gastrointestinal tract, and apparatus for use therewith, by inventor Uday Devanaboyina teaches a wearable, portable EMG system for long term home use, but does not teach a plurality of electrode array based wireless patches to cover the entire GI tract.

Additionally, wireless, wearable, home-use based ECG heart monitoring devices are well known in the art. For example, Biotronik US patent application 20130046150, teaches "Long-term cutaneous cardiac monitoring". The system disclosed is for long-term heart monitoring via a disposable adhesive surface patch for cutaneous mounting with built-in electrodes and wireless communication with a remote service center. However, the nature of cardiac heart muscle tissue signals is very different than that of the Gastrointestinal system, and thus, the patent does not teach about grids of electrodes or complex aggregate spatiotemporal data analysis. Cardiac systems typically require only two or three electrode pairs, and individual heart beats are analyzed or monitored, rather than aggregate heart beat data.

Furthermore, numerous examples of small, disposable, wireless, adhesive wearable medical EMG data collection patches exists in the marketplace. For example, DELTA Danish Electronics, Light & Acoustics, Inc., Denmark, has developed an ePatch® system for home health monitoring. (http://epatch.madebydelta.com). While this system and others are examples of the growing trend of wearable medical devices, it does not teach beyond the well known EGG medical practices-few electrodes, primarily for monitoring purposes, and analyzed linearly rather than aggregately. No suggestion is made for full GI track monitoring by arrays of electrodes over long time periods for advanced spatiotemporal data pattern analysis.

Additionally, there are numerous research papers exploring the use of wireless EMG and EGG systems for home health monitoring. For example, S. Haddab, et al, proposes a "Microcontroller-Based System for Electrogastrography Monitoring Through Wireless Transmission" system. However, like all other commercial and scientific EGG efforts, his efforts are short term (four hours maximum), and with a minimum of traditional electrodes. No suggestion of multi-day recording is made. The mathematical analysis was of the traditional type designed to remove noise and artifact from the linear signal, rather than achieve diagnostic successes through spatiotemporal pattern analysis of data aggregated from in-situ subjects over multi-day periods.

The same is true of Haahr, R. G., et al, who despite their promising work on "A wearable 'electronic patch' for wireless continuous monitoring of chronically diseased patients", they specifically teach a "wearable health system . . . made as an electronic patch . . . (and) for the EMG application three standard dry silver electrodes are used separated by 10 mm."

U.S. Pat. No. 7,593,768, "Detection of smooth muscle motor activity", discloses EMG peak detection in the frequency spectrum and calculating the energy of the peaks for the stomach and small Intestine using internal and surface electrodes. It does not teach towards the presently disclosed invention. Specifically, only mention of the recording time involved a maximum time of two hours, and the maximum number of electrodes mentioned was eight. Furthermore, these eight electrodes were implanted, not external, and their data was summed up into one time series, not analyzed as a spatial temporal pattern. Nor is there any mention of wearable or wireless data collection for ambulatory, at home data collection.

While there is a long history of minor success with EGG approaches, and EGG/EEnG possesses important information regarding the physiological and functional state of the GI tract, the cost and limited diagnostic benefit has so far prevented the mainstream and large scale medical mainstream use of EGG and EEnG.

Furthermore, there is enormous variability in the anatomical nature and structure and organ placement and tissue densities among patients. There is also enormous variability in both the healthy and disordered GI tract slow muscle rhythmic activity physical parameters and patterns. These two factors prevent any kind of EMG electrode placement standardization, and limit the effectiveness of EMG in diagnosing the large number of different GI tract disorders commonly encountered in the clinical setting.

Thus, it is an objective of the present invention to create a system that places enough of an array of particularly arranged electrodes over larger GI tract areas, or the entire GI tract, to obviate the issues caused by non-standard electrode placements or individual anatomical variability.

It is not suggested herein that any one particular electrode array placement patterns is the focus or limit of the presently disclosed invention. There exist an almost infinite variety of different electrode arrangements, some of which will possess differing pros and cons with regards to optimization of cost versus data collection versus additional engineering, diagnostic, and business consideration.

It is instead suggested that by having any plurality of variously spaced, orthogonally arranged bipolar electrode pairs on a patch, with one or more patches covering the entire, or large part, of one or more digestive organs, sufficiently ideal diagnostic data sets can be collected, throughout a single days normal digestive activities, (a single "gnt beat"), for sufficient mathematical post-processing to yield great diagnostic value. Furthermore, by employing multiple electrodes and patches, it is also possible to dynamically alter which electrodes form bipolar pairs based on incoming data optimization algorithms. Importantly, a plurality of smaller patches, rather than one single giant patch, is an ideal embodiment because smaller patches help prevent significant lateral movement of electrodes on the skin.

In addition to the previously mentioned limitations of standard EGG, there are many sources of data variability, including patient height, weight, anatomy, skin condition, recent food consumption history, metabolic rest state, and the like.

Furthermore, data variability is additionally introduced from highly variable placement of electrodes or patches, or in equipment manufacturing variations, and of course the variability caused by different disorders and the general chaotic and nonlinear dynamic nature of biological systems. These large variations negatively impact diagnostic effectiveness of all previous known systems. This variability problem is compounded further by the fact that EGG is a lower amplitude signal compared to other bodily electrophysiological signals, such as the heartbeat or breathing, and thus easily influenced by both random sources of variation and systematic influence factors.

It is thus an objective of the presently disclosed invention to effectively avoid these limitations by use of the presently disclosed patches, in combination with continual or intermittent data collection and transmission over periods of many hours, days, in combination with advanced mathematical techniques, in both the time and frequency domains.

The usual 24 hour circadian cycle of the body is well representative of the digestive cycle of the normal or healthy body. Research has shown that the digestive system follows a similar 24 hour pattern, with low GI activity during sleep, increased activity after waking and temporary increases following breakfast and other meals, with defecation often occurring at more or less the same time each day. This full cycle of GI activity might be called a "gut beat" in analogy to the heartbeat cycle of the heart.

Inasmuch as there are events such as Giant Migrating Contractions (GMC's) and Migrating Motor Complexes (MMC's) associated with propulsion of the contents of the intestines that occur on the order of a few to several times per gut beat, capturing data for at least one full day is essential to develop an understanding of the workings of an individual's digestive system with the intent to diagnose abnormality. In fact due to normal variability it is further advantageous to sample for several days to better quantify infrequent events, capture rare events, and reduce statistical noise in the measurement of common events.

An example of a common event is the increase in degree of muscular activity in any of the stomach, small intestine or colon after a meal. In general all these organs respond to meal ingestion either within minutes or tens of minutes, and quantifying that increase has diagnostic value. An example of an uncommon event is limited propulsion of the luminal contents of the small intestine, which typically happen several times per day in healthy subjects. An example of a rare event is defecation, which happens on average once per day for healthy subjects, but for patients with constipation it may only happen once every several days.

Thus, we would characterize this combination of multiple patches of multiple electrode pair arrays designed to sample, store, and wirelessly transmit data intermittently to remote computer servers over a larger segment of time, as the collection of spatio-temporal electromyographic data. And while there are an infinite number of ways for the remote servers to mathematically and algorithmically analyze and display said aggregates of such large data sets, the presently ideal embodied invention utilizes techniques such as time series analysis, time-dependent frequency analysis, and pattern matching analysis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

SUMMARY

One aspect of the present disclosure is directed to a wearable non-invasive wireless electrodiagnostic patch system for profiling gastrointestinal tract muscular activity of a subject. The system comprises a set of electromyographic-sensing patches adapted for multi-day constant attachment to the skin surface of the midsection of a subject; each patch of said set comprising a particularly arranged array of bipolar electrode pairs; each patch enabled for collecting, storing, processing, and communicating a range of full to partial time segments of sensed spatiotemporal electromyographic signals from the subject to remote computing and display devices. Said computing devices are configured to mathematically and algorithmically process and analyze aggregated amounts of said spatiotemporal electromyographic signals to yield visually displayable, diagnostically-valuable physiological parameters of gastrointestinal smooth muscle electrical activity of said subject In some embodiments of the particularly arranged array of bipolar electrode pairs, the distribution and orientation pattern allows for a maximum number of electrodes pairs to be arranged substantially orthogonally to each other in order to better sense signals originating from any orientation or location In some embodiments, said parameters comprise any of frequency, amplitude, power, or periodicity of electrical activity, as well as periodicity of larger time frame patterns of electrical activity, said parameters further assignable to a region of the gastrointestinal tract.

In some embodiments, the communicating of said patches EMG data to said remote computing devices occurs wirelessly, selected from the group consisting of Bluetooth, Wi-Fi, cellular, infrared, and the like.

In some embodiments, said patches are selected from the group: designed to be used as a larger number of smaller patches, to cover a large portion of the GI tract, so as to minimize lateral slippage and movement of electrodes; designed so each electrode pair is aligned radially; designed so each electrode pair is aligned along a circumferential line; designed so one electrode is a ground electrode and is configured to pair with a plurality of active electrodes, each pairing representing a bipolar electrode pair; and designed so the ground electrode is disposed centrally within a circumferential arrangement of the plurality of active electrodes.

In some embodiments, each of the EMG-sensing patches comprises a memory capacity sufficient to store accumulated signal for a period of up to at least one hour.

In some embodiments, the networked computing device comprises one or more data analysis applications, said applications configured to analyze data transmitted to it from the local electronic device, and said data analysis is selected from the group comprising: individuation of processed data according to unique identifiers with which data coming from each patch is tagged; desired signal isolation based on subtraction or relative weighting of patterns ascribable to sources other than gastrointestinal smooth muscle; comprises inclusion of data directly entered into the local electronic device by the patient; comprises inclusion of data entered directly into a computing device by a healthcare professional; and comprises recognition of each EMG-sensing patch according to a coordinate-mapped location on the body of the patient.

In some embodiments, the mathematical and algorithmic analysis of said aggregated large data sets is selected from the group including: time series analysis, time-dependent frequency analysis, and pattern matching analysis.

In some embodiments, the subject includes both humans and animals, and said diagnostically-valuable physiological parameters are valuable for both diagnosing GI tract diseases, and diagnosing the effects of various foods, pharmaceutical drugs, and other substances on GI tract activity and health.

In some embodiments, said subject is enabled in a manner selected from the group: being able to go about their daily lives; being able to manually enter consumed food descriptions into their medical records via portable, desktop, and handheld computing devices; being able to manually enter qualitative or quantitative values of GI pain and its location, bloating, nausea and other disease symptoms experienced and their time experienced; being able to take pictures of meals to be consumed as additional data to be included in the analysis; being able to take pictures of meals to be consumed, with automated interpretation of nutritional content, as additional data to be included in the analysis; and being able to record still pictures, audio and video messages that are entered into their medical records.

In some embodiments, the system further comprises additional sensors selected from the group consisting of: accelerometers, motion sensors, position sensors, heart rate sensor, blood pressure meter, respiration rate, blood oxygen levels, body temperature, galvanic skin response, skin-electrode impedance, electrode-electrode impedance, accelerometers, audio microphones, photography, videography, ECG, and EEG.

Another aspect of the present disclosure is directed to a low-cost, non-invasive method of profiling gastrointestinal tract muscular activity of an ambulatory patient. The method comprises: placing at least one EMG-sensing patch on a skin surface of the patient proximate the gastrointestinal tract, said EMG-sensing patch comprising particularly selected arrays of bipolar electrode pairs; acquiring electrical signals from one to all regions of the gastrointestinal tract with at least some subset of said plurality of electrode pairs arranged as arrays on each individual patch; acquiring electrical signals from one or more regions of the gastrointestinal tract with at least some subset of said plurality of said EMG-sensing patches; acquiring electrical signals at intervals ranging from intermittently to continuously from ambulatory patients living and behaving normally over at least a substantial portion of one day; wirelessly transmitting said acquired electronic signal data to nearby networked computing devices; and collecting, transmitting, and mathematically processing the acquired aggregated signals on any of the said computing devices to yield and display physiological parameters of gastrointestinal electrical activity collected from patients.

Another aspect of the present disclosure is directed to a non-invasive, wearable, low-cost full GI tract electrodiagnostic device and method. The device and method comprises: a plurality of electromyographic-sensing wearable patches covering substantially all of the GI tract, said patches adapted for placement on the skin surface of the midsection region of a subject, said patches optionally available in a variety of sizes, shapes, and bipolar electrode densities and array distribution configurations. Each said patch comprises at least one bipolar electrode pair, and said patch is additionally enabled for intermittent to continuous, wireless communication of a signal indicative of a sensed, recorded, electromyographic signal. Said electrodes are linked to an electronic devices, wherein said electronic devices include: amplifier circuits, band pass filter circuits, analog to digital converter circuits, memory circuits, wireless data transmission circuits and associated antenna, a light, ultra-compact power source, and a water-resistant housing. Said housing is made for multi-day adherence to said subjects body, and said electronic device is in wireless communication with networked computing devices. Said networked computing device is configured to utilize advanced mathematical and algorithmic processes to analyze aggregate signals received from the local electronic device in order to yield remotely viewable physiological parameters of gastrointestinal smooth muscle electrical activity for the purposes of diagnosis and treatment of GI disorders.

The networked computing device comprises one or more data analysis applications, said applications configured to analyze data transmitted to it from the local electronic device. Embodiments of the present invention include a system wherein data analysis comprises individuation of processed data according to unique identifiers with which data coming from each patch is tagged. Embodiments of the present invention also include the system wherein data analysis comprises desired signal isolation based on subtraction or relative weighting of patterns ascribable to sources other than gastrointestinal smooth muscle. In this and other embodiments, the patterns ascribable to sources other than gastrointestinal smooth muscle are identifiable through comparison of relative strength of signals from EMG-sensing patches, the patches identified per their location on the skin surface relative to an underlying gastrointestinal tract region.

Further embodiments of the present invention include a system where the data analysis comprises identification of signal peaks related to each other, wherein related peaks may occur at either the same or at different frequencies. In this and other embodiments, the data analysis comprises subjecting data to a Fast Fourier Transformation algorithm at one or more sample lengths, said algorithm directed toward identification of peaks with optimal signal to noise ratio and optimal signal strength. Further embodiments of the present invention include data analysis comprising integral wavelet transform analysis. Still further embodiments of the present invention include data analysis comprising pattern analysis, wherein received data are compared against examples of known patterns. Additional embodiments of the present invention are systems where the data analysis comprises a search for non-sinusoidal patterns through a pattern-matching algorithm.

The system of the present invention includes those wherein data analysis comprises inclusion of data directly entered into the local electronic device by the patient or a healthcare professional. Another embodiment of the present invention is a system wherein data analysis comprises inclusion of data entered directly into a computing device by a healthcare professional.

Another embodiment of the system of the present invention is where data analysis comprises recognition of each EMG-sensing patch according to a coordinate-mapped location on the body of the patient. In this and further embodiments of the present invention the coordinate-mapped depiction of the location on the body of the patient comprises a map having a 2-dimensional planar view of the surface of the body. Additional embodiments are wherein the coordinate-mapped depiction of the location on the body of the patient comprises a 3-dimensional model of the body. A further embodiment is the system of the present invention, wherein the coordinate-mapped depiction of the location on the body of the patient comprises further data related to the positioning of the gastrointestinal tract of the patient.

BRIEF DESCRIPTION OF THE DRAWINGS

Various embodiments of the invention are disclosed in the following detailed description and accompanying drawings. Other features and advantages of the invention will become apparent from the following detailed description in conjunction with the drawings, wherein:

FIG. 1 schematically illustrates the preferred embodiment of the entire wearable, wireless, GI electrodiagnostic data aggregating and diagnostic system;

FIG. 2 shows a bottom view of a multi-electrode configuration of the disposable unit 100, shown with its corresponding electronic controller detached and spaced from the disposable unit 100;

FIG. 3 provides a simplified bottom view of a patch, and FIG. 1B provides a simplified bottom view, of a wearable, disposable/recyclable unit 100 and an electrode patch EMG circuit 200 and it's array of nine bipolar electrodes 205 as an exemplary example of the invention;

DETAILED DESCRIPTION OF THE DRAWINGS

Figure 4:
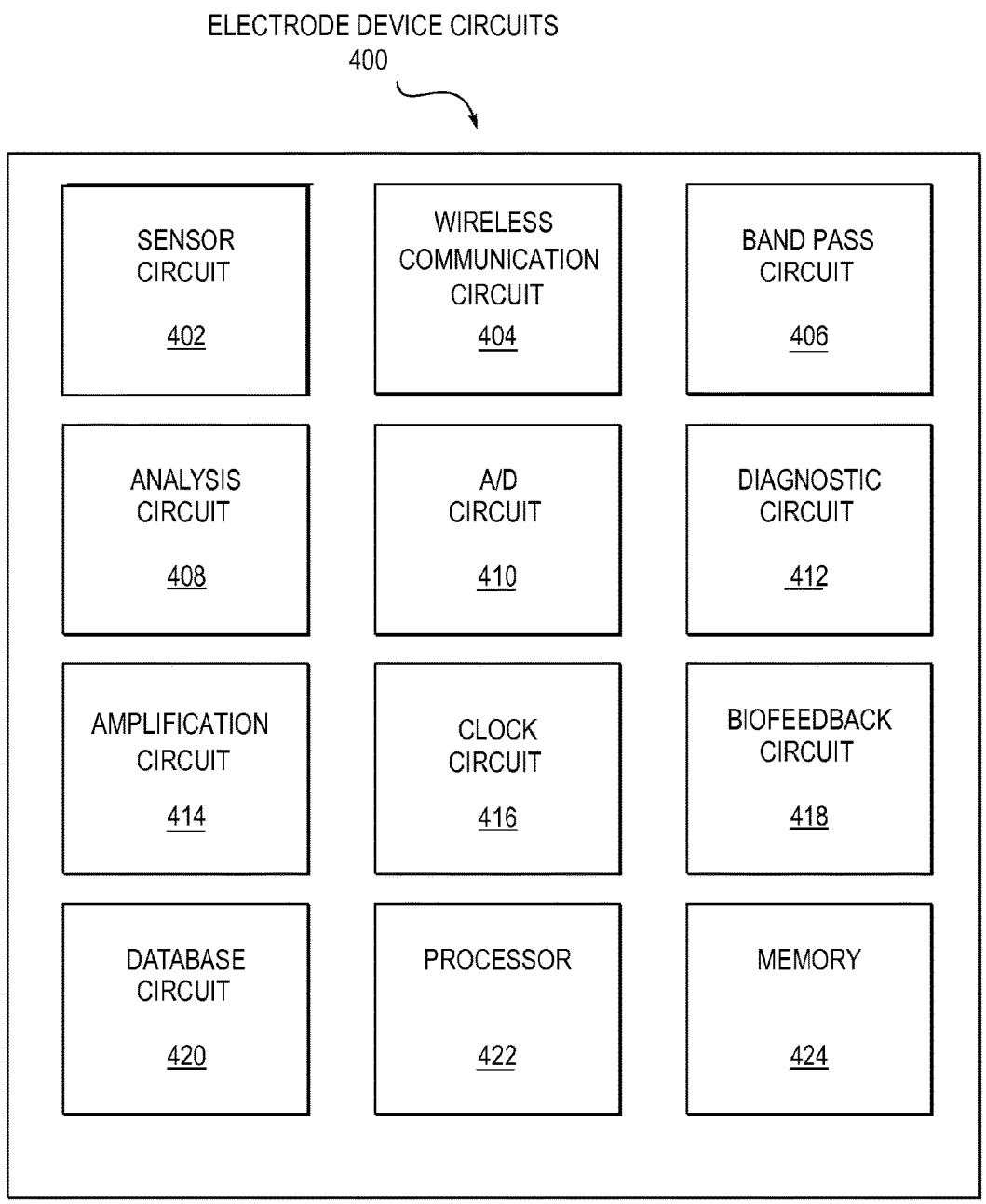
FIG. 4 illustrates a functional view of a system 200 with various circuit modules including a processor and memory to run the software.

The following description is of preferred versions of the invention, and the invention is not limited to these preferred versions. The scope of the invention should be determined with reference to the claims set forth at the end of this document.

FIG. 1 schematically illustrates the preferred embodiment of the entire wearable, wireless, GI electrodiagnostic data aggregating and diagnostic system, including hand held computing devices 160a for easy patient 150 supplemental data entry, and remote computer display devices 160c for patch 300 wireless transmission 130 in order for remote computer servers 160b to process for display the GI tract 110 physiological parameters 120 for doctor diagnostic assistance.

Figure presents a system wide view, with a set of multi-day-wearable patches 300/200 that sense, amplify and digitize myoelectric data 120 at the skin surface 150 originating in the smooth muscles of the stomach, small intestine and colon, 110 and transfer the data wirelessly 130 to a handheld computing device 160a, the patches having two or more bipolar pairs of electrodes 205 arranged substantially orthogonally, the patches further having onboard sensors that are capable of measuring any of acceleration, velocity or position 402; the computing device further capable of allowing the patient to enter 420 information 160a relevant to their gastrointestinal (GI) tract such as meal contents, bowel movements or abdominal pain, synchronizing and combining this information with the time-stamped 416 raw data 120 and uploading both to a cloud server 160b or other wireless host; the host serving as a repository for further processing or download to a processing device, the processing device using time and frequency based algorithms to extract events and patterns of events that relate to the activity of the aforementioned GI organs 120, specifically slow waves that are associated with mixing and propulsion of their contents as part of digestion and elimination, with the purpose of providing diagnostic information on the activity of the organs as they relate to functional GI disorders (FGIDs) such as irritable bowel disorder (IBS). The computing device further having the ability to coordinate data transfer schedules with the patches to accommodate either regularly scheduled transfers 404 or reconnecting when temporarily out of range, and the further ability to identify patches individually.

FIG. 2 schematically illustrates the electrode array circuit board 200. The disposable unit 200 has at least two, but preferably eight embedded bipolar pair electrodes 205 arranged in an array 220. Preferably, the inter-electrode distance is between 1 and 2 inches. The electrodes 205 are embedded inside the printed circuit board patch unit 200, with an ideally slight extension for greater skin contact. The circuit board 200 will likely be entombed in waterproof resin for greater water resistance, and the patch housing itself 300 will ideally have water resistant properties.

FIG. 3 shows a bottom and top view of an exemplary patch 300 and electrode array circuit board 200. Long-term non-invasive GI tract monitoring, an inexpensive, light, water resistant and disposable skin-adhesive unit 100 is provided. Because the unit is disposable, it can be easily replaced with another disposable unit after its usage for a few days. The bottom of the disposable unit 100 has an adhesive surface 110 that can be affixed to the patient's skin for at least 7 days. One exemplary type of such adhesive material is the pressure-sensitive adhesive which forms a bond when pressure is applied to stick the adhesive to the adherent (e.g., the patient's skin).

Figure 5:
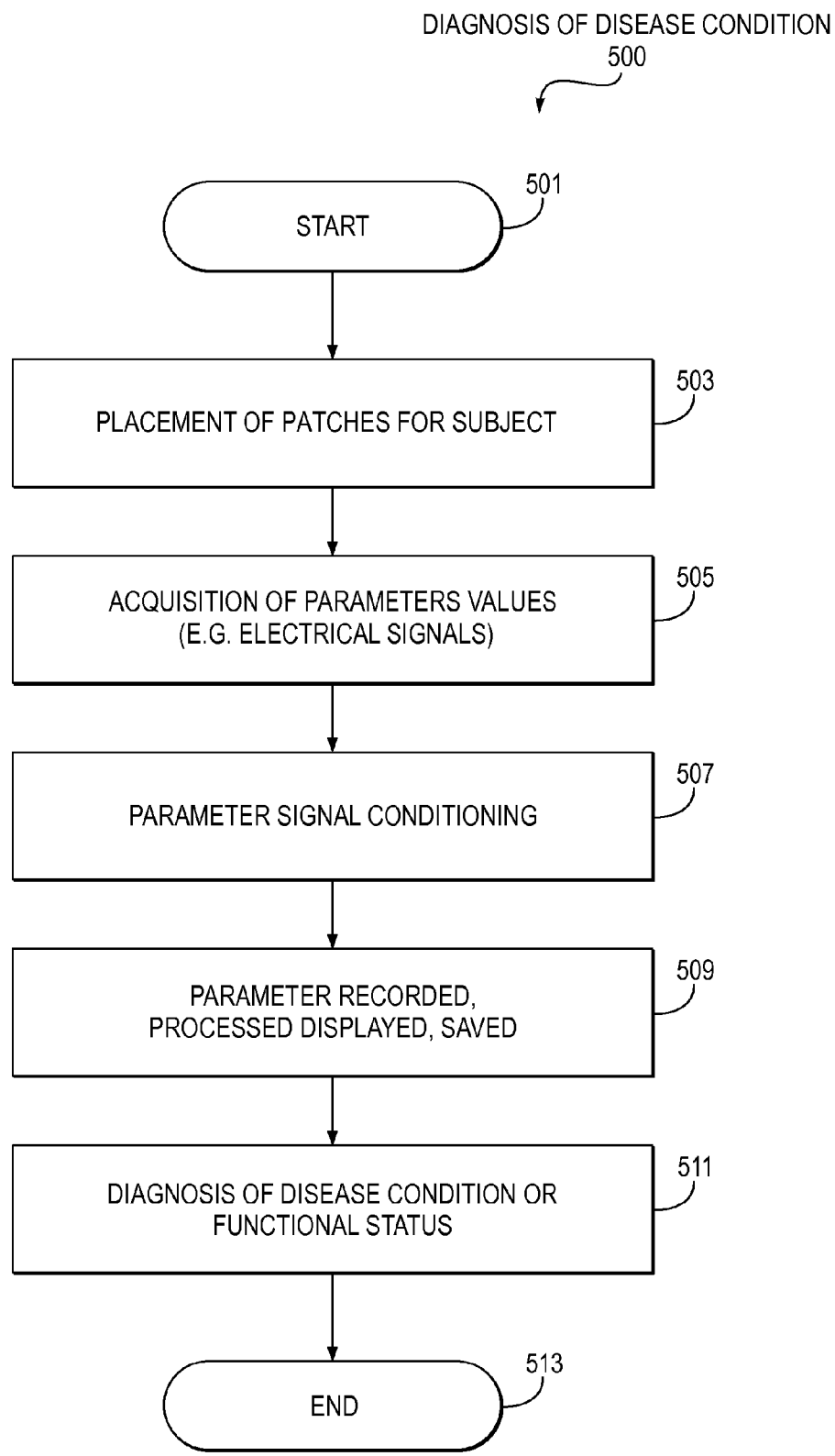
FIG. 5 is a flow chart of the diagnosis process of typical GI disease condition 500.

FIGS. 4 and 5 illustrates flow charts and functional views of the system when in use.

Figure 6:
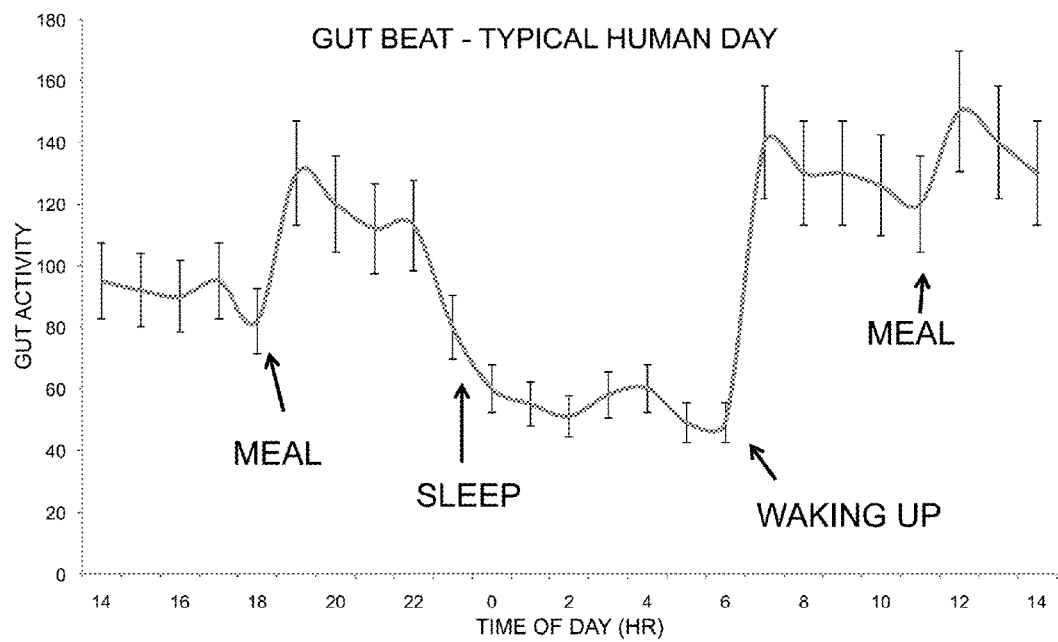
FIG. 6 is a data chart of the typical human daily "Gut Beat", or GI tract activity of a normally behaving person, which is the ideal minimum sample period for maximum GI disorder diagnostic functionality of the presently disclosed invention.

FIG. 6 is a data chart of the typical human daily "Gut Beat", or GI tract activity of a normally behaving person, which is the ideal minimum sample period for maximum GI disorder diagnostic functionality of the presently disclosed invention.

DETAILED DESCRIPTION OF THE PREFERRED EMBODIMENT

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

Typical embodiments of a local computing device are sized to be handheld or generally portable. This physical aspect of the device is appropriate for the operation of the system simply because the patient needs to have this local device with himself or herself, or very close at hand, at least substantially throughout the duration of the monitoring period. Typical examples of a local computing device, per currently available technology, include mobile telephones, personal digital assistants, and tablet devices.

Embodiments of a local computing device can communicate through wireless networks by way of cell phone frequencies, satellite communication frequencies, wifi networks, or any network that can form a communication route to a networked computing device. Wireless transmission of data to a networked computing device may occur by way of an intervening remote data storage server, such server often referred to generically as "the cloud".

Electromyography is a general term for acquiring or monitoring signals as emanated from physiological sources. Electromyography as applied particularly to the smooth muscle of the gastrointestinal tract from the GI tract can also be termed electrogastrography or electroenterography.

Embodiments of the disclosed system and methods may be applied toward monitoring the electrical activity of the gastrointestinal tract of human subjects of any age, including infants, children, adolescents, and adults. Embodiments may also be applied to monitoring the electrical activity of the gastrointestinal tract of non-human animals, non-human mammals in particular.

Bluetooth LE is a current example of a low energy transmission capability appropriate for operation of the disclosed technology. Other low energy electronic communication protocols that may be developed in the future are included as embodiments. The low energy aspect of communication that the EMG-sensing patches makes use contributes to the ability of a battery to sustain operation of the patches for sustained periods of operation, such as 24 hours or more of continuous monitoring.

An intermittent schedule of signal transmission or transmitting in response to a query is a feature that conserves battery power, and contributes to the ability of a battery to sustain operation of the patches for sustained periods of operation, such as 24 hours or more of continuous monitoring.

Additionally, each Bluetooth enabled patch will possess a unique identifier, so that the EMG sensing patches are able to transmit a unique identifier to the local computing device. This will allow identification of individual patches—both those located on one patient, or those located on different patients or subjects in the same general vicinity.

The unique identifier term, as used herein, generally refers to a serial number, an arbitrary number, or an accession number that is applied to it by the system or by a human operator. This identifier does not necessarily include any locational information per se, although locational information could be associated with the identifier by a human operator or by an aspect of the system.

It is also advantageous for the operation of the patch that the battery has a high charge capacity. Additionally, embodiments of the technology include any future technological advancements that may be made regarding recharging of batteries, particularly by way of induction or solar power.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

The invention claimed is:

1. A wearable, non-invasive wireless electrodiagnostic system for profiling gastrointestinal tract activity of an ambulatory patient,
the system comprising:
an electromyographic-sensing patch adapted for multi-day constant attachment to a skin surface of a midsection of a patient, the patch comprising:
an array of bipolar electrode pairs comprising two or more bipolar electrode pairs, wherein each individual electrode of the bipolar electrode pairs comprises an electrode-specific identifier, and a ground electrode is disposed centrally within a circumferential arrangement of a plurality of active electrodes,
wherein information in the patch is integrated and dynamically combined such that the pairing between each of the electrodes that form each bipolar pair and the corresponding data obtained from the array of bipolar electrode pairs are combined based on incoming data optimization algorithms, and
wherein the incoming data optimization algorithms comprise one or more of: time series analysis, time-dependent frequency analysis, and pattern matching analysis of spatio-temporal electromyographic data derived from the array of bipolar electrode pairs; and
a circuit board having a battery and a processor with instructions stored in memory,
wherein implementation of the instructions causes the processor to identify individual electrodes via the electrode-specific identifier, receive signals from the array of bipolar electrode pairs over a period of at least one day, amplify and digitize the electromyographic data from the signals, and transmit data to at least one of a remote computing device or a networked computing device.

2. The wearable, non-invasive wireless electrodiagnostic system of claim 1, wherein the array of bipolar electrode pairs comprises eight active bipolar electrodes forming four bipolar pairs.

3. The wearable, non-invasive wireless electrodiagnostic system of claim 1, wherein the array of bipolar electrode pairs comprises two parallel pairs of bipolar electrodes and an orthogonal pair of bipolar electrodes.

4. The wearable, non-invasive wireless electrodiagnostic system of claim 1, wherein the patch comprises a memory capacity sufficient to store accumulated signal for a period of up to at least one hour.

5. The wearable, non-invasive wireless electrodiagnostic system of claim 1, further comprising one or more sensors selected from the group consisting of: an accelerometer, motion sensor, position sensor, heart rate sensor, blood pressure meter, respiration rate sensor, sensor to detect blood oxygen levels, body temperature sensor, galvanic skin response sensor, skin-electrode impedance sensor, electrode-electrode impedance sensor, electrocardiogram sensor, electroencephalogram sensor, audio microphone, camera, and video.

6. The wearable, non-invasive wireless electrodiagnostic system of claim 1, further comprising the remote computing device, wherein the remote computing device is further configured to mathematically and algorithmically process and analyze aggregated amounts of spatiotemporal electromyographic signals to yield visually displayable, diagnostically-valuable physiological parameters of gastrointestinal smooth muscle electrical activity of the patient.

7. The wearable, non-invasive wireless electrodiagnostic system of claim 1, wherein the patch comprises one or more patches and the system further comprises the remote computing device, wherein communication between the one or more patches and the remote computing device occurs wirelessly using one or more of Bluetooth, Wi-Fi, cellular, and infrared.

8. The wearable, non-invasive wireless electrodiagnostic patch system of claim 1, further comprising the remote computing device, wherein the remote computing device is further configured to receive user inputs from the patient providing information regarding one or more of: meal contents, bowel movements, physical activity, and abdominal pain and synchronize and combine the information with time-stamped electromyographic data.

9. The wearable, non-invasive wireless electrodiagnostic system of claim 1, further comprising the remote computing device, wherein the remote computing device is further configured to execute time and frequency-based algorithms to extract events and patterns of events related to activity of gastrointestinal organs.

10. The wearable, non-invasive wireless electrodiagnostic system of claim 1, wherein the instructions stored in memory cause the processor to receive the signals intermittently from the array over the period.

11. The wearable, non-invasive wireless electrodiagnostic system of claim 1, wherein the patch is configured to sense electromyographic signals originating in smooth muscles of a stomach, a small intestine, and a colon.

12. The wearable, non-invasive wireless electrodiagnostic system of claim 1, wherein the system comprises a plurality of greater than one patch positioned on the patient.

13. The wearable, non-invasive wireless electrodiagnostic system of claim 1, wherein the patch is water-resistant and the circuit board is waterproof.

14. The wearable, non-invasive wireless electrodiagnostic system of claim 1, wherein the patch includes a pressure-sensitive adhesive configured to adhere to the skin surface for more than one day.

15. The wearable, non-invasive wireless electrodiagnostic system of claim 1, wherein the battery is configured to sustain operation of continuous monitoring for a time period of at least 24 hours.

16. The wearable, non-invasive wireless electrodiagnostic system of claim 1, further comprising the remote computing device, wherein the remote computing device comprises a data analysis application configured to isolate a desired signal from the transmitted data, the analysis application selected from the group consisting of: individuation of processed data according to unique identifiers, isolation based on subtraction of patterns ascribable to sources other than gastrointestinal smooth muscle, isolation based on weighing relative signal strength ascribable to sources other than gastrointestinal smooth muscle, detection of signal peaks at same or different frequencies, fast Fourier transformation to optimize signal to noise ratio and signal strength, wavelet transform analysis, pattern analysis, search for non-sinusoidal patterns, 2-dimensional co-ordinate mapping of the signal on a body of the patient, 3-dimensional co-ordinate mapping of the signal on the body of the patient, co-ordination of signal with position of the gastrointestinal tract of the patient, and combinations thereof.

* * * * *